United States Patent
Camus et al.

(10) Patent No.: US 7,623,622 B2
(45) Date of Patent: Nov. 24, 2009

(54) X-RAY SYSTEM WITH AN ADJUSTMENT-ACQUISITION DEVICE

(75) Inventors: Estelle Camus, Mountain View, CA (US); Michael Maschke, Lonnerstadt (DE); Thomas Redel, Poxdorf (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/805,819

(22) Filed: May 24, 2007

(65) Prior Publication Data

US 2007/0274449 A1    Nov. 29, 2007

(30) Foreign Application Priority Data

May 29, 2006 (DE) .................. 10 2006 024 973

(51) Int. Cl.
  *G01N 23/04* (2006.01)
(52) U.S. Cl. ........................... 378/62; 378/108
(58) Field of Classification Search ............ 378/97, 378/95, 98.7, 108, 110, 112, 62
See application file for complete search history.

(56) References Cited

U.S. PATENT DOCUMENTS

| | | | |
|---|---|---|---|
| 6,661,240 B1 | 12/2003 | Johnson et al. | |
| 2002/0039403 A1* | 4/2002 | Oota | 378/196 |
| 2002/0163994 A1 | 11/2002 | Jones | |
| 2006/0002513 A1* | 1/2006 | Bernhardt et al. | 378/97 |
| 2007/0031018 A1 | 2/2007 | Camus et al. | |
| 2007/0041625 A1 | 2/2007 | Camus et al. | |
| 2007/0116180 A1* | 5/2007 | Omernick et al. | 378/116 |

FOREIGN PATENT DOCUMENTS

| | | |
|---|---|---|
| DE | 102004031681 A1 | 1/2006 |
| DE | 102005036564 A1 | 2/2007 |
| DE | 102005039189 A1 | 2/2007 |
| EP | 0993804 A1 | 4/2000 |
| EP | 1034738 B1 | 9/2000 |

* cited by examiner

*Primary Examiner*—Hoon Song

(57) ABSTRACT

A recording arrangement of an x-ray system comprises an x-ray source and an x-ray detector. Adjustment parameters can be manually supplied to the recording arrangement by an operator of the x-ray system, so that the x-ray source emits x-rays according to the manually given adjustment parameters and the x-ray detector accordingly acquires a sequence of images of an object. The manually supplied adjustment parameters can be automatically acquired by an acquisition device and stored in a remanent memory at least temporarily assigned to the acquisition device and remain stored after the completion of the acquisition of the sequence independently of a further operation of the x-ray system. The stored adjustment parameters can be retrieved from the remanent memory by the operator and supplied again to the recording arrangement so that a further sequence of images can be acquired according to the retrieved adjustment parameters.

17 Claims, 6 Drawing Sheets

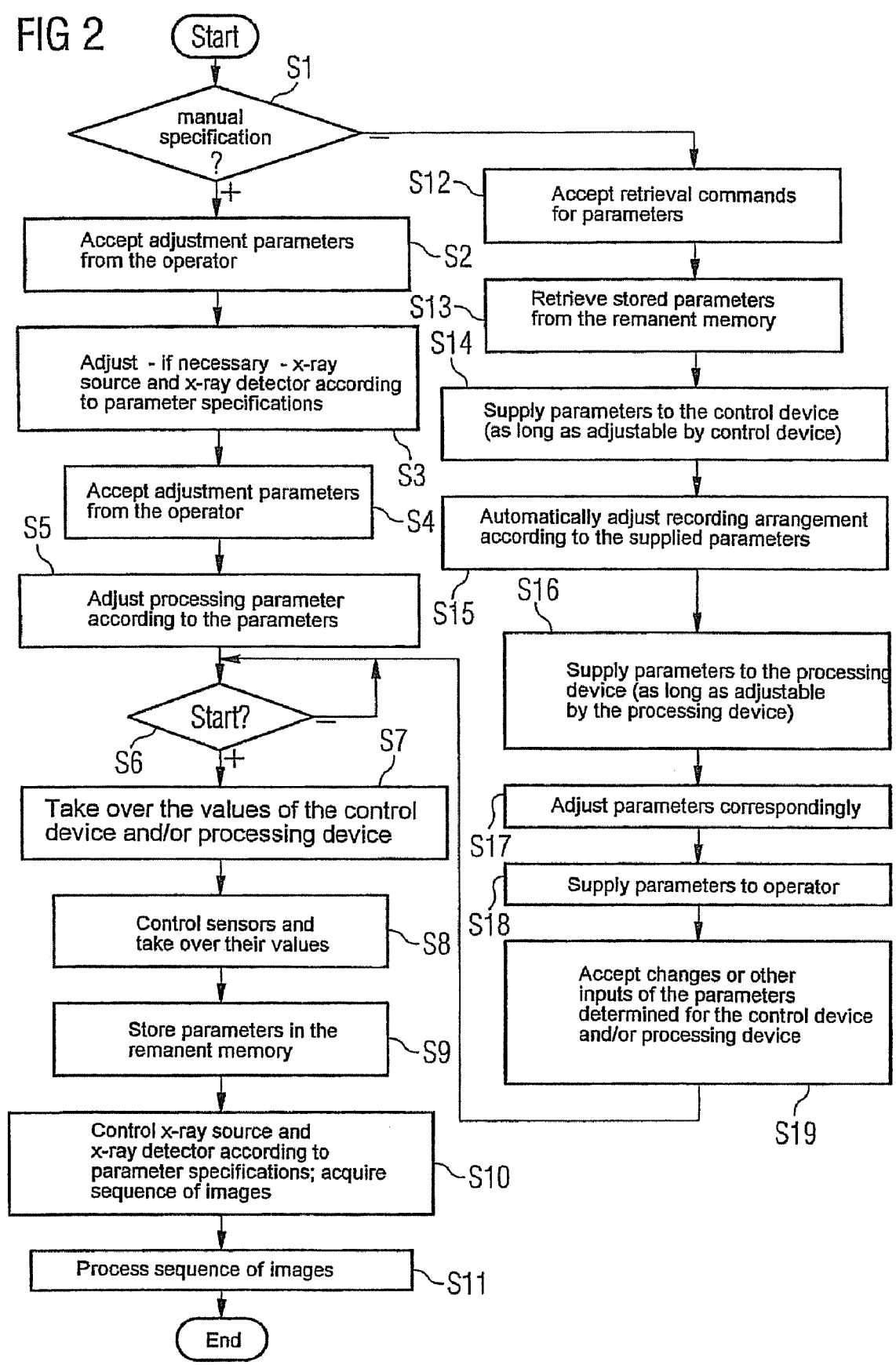

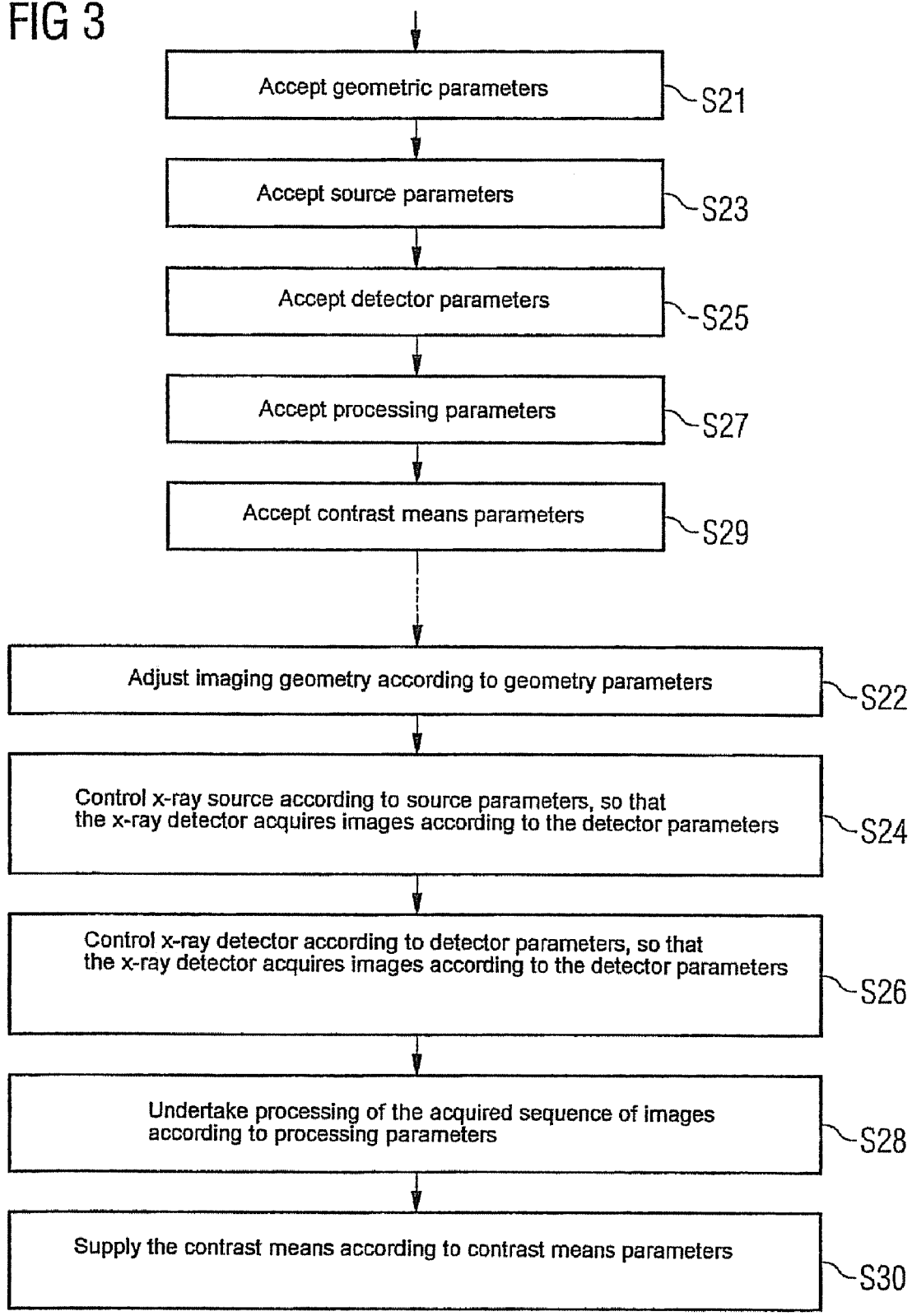

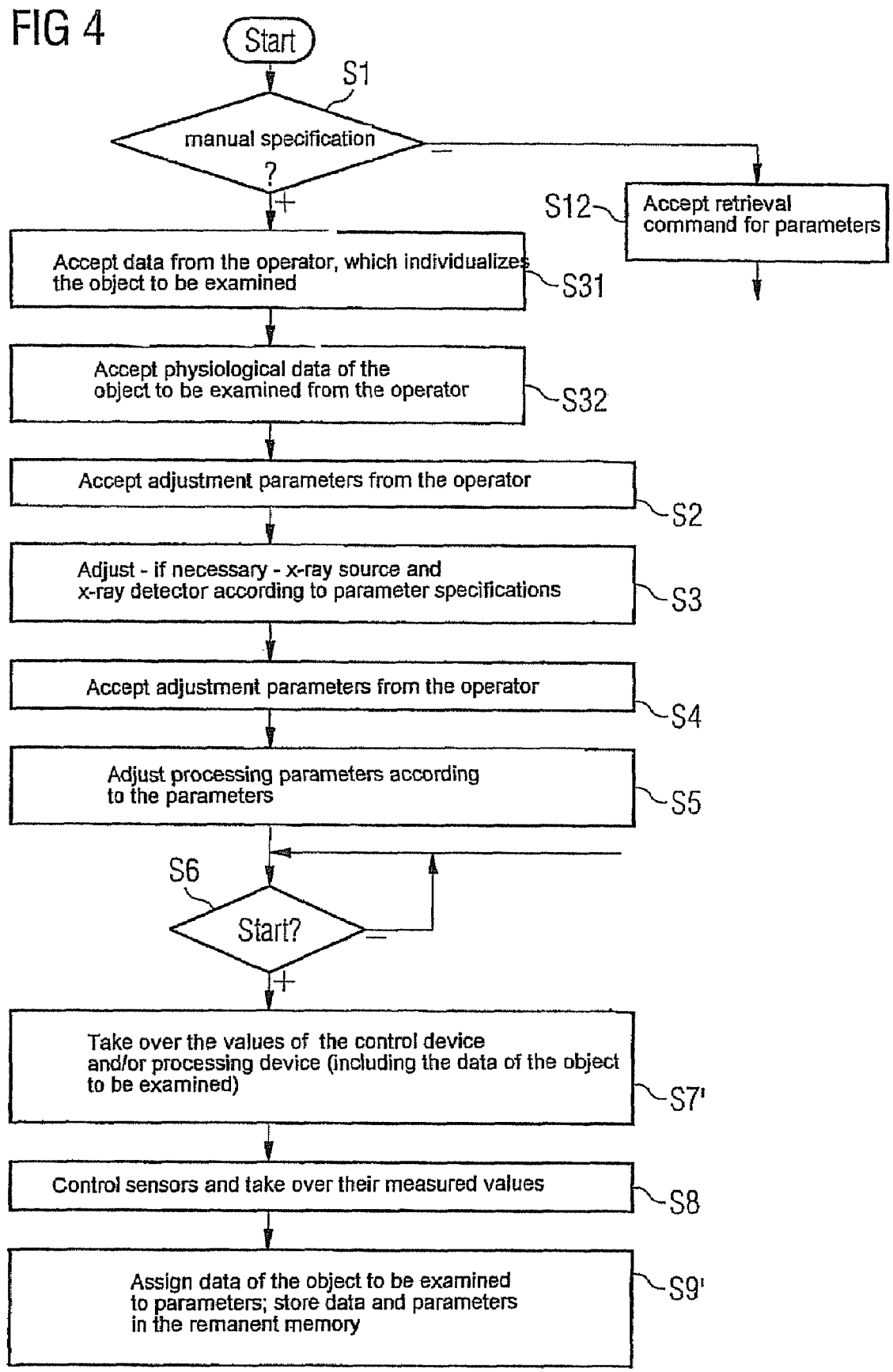

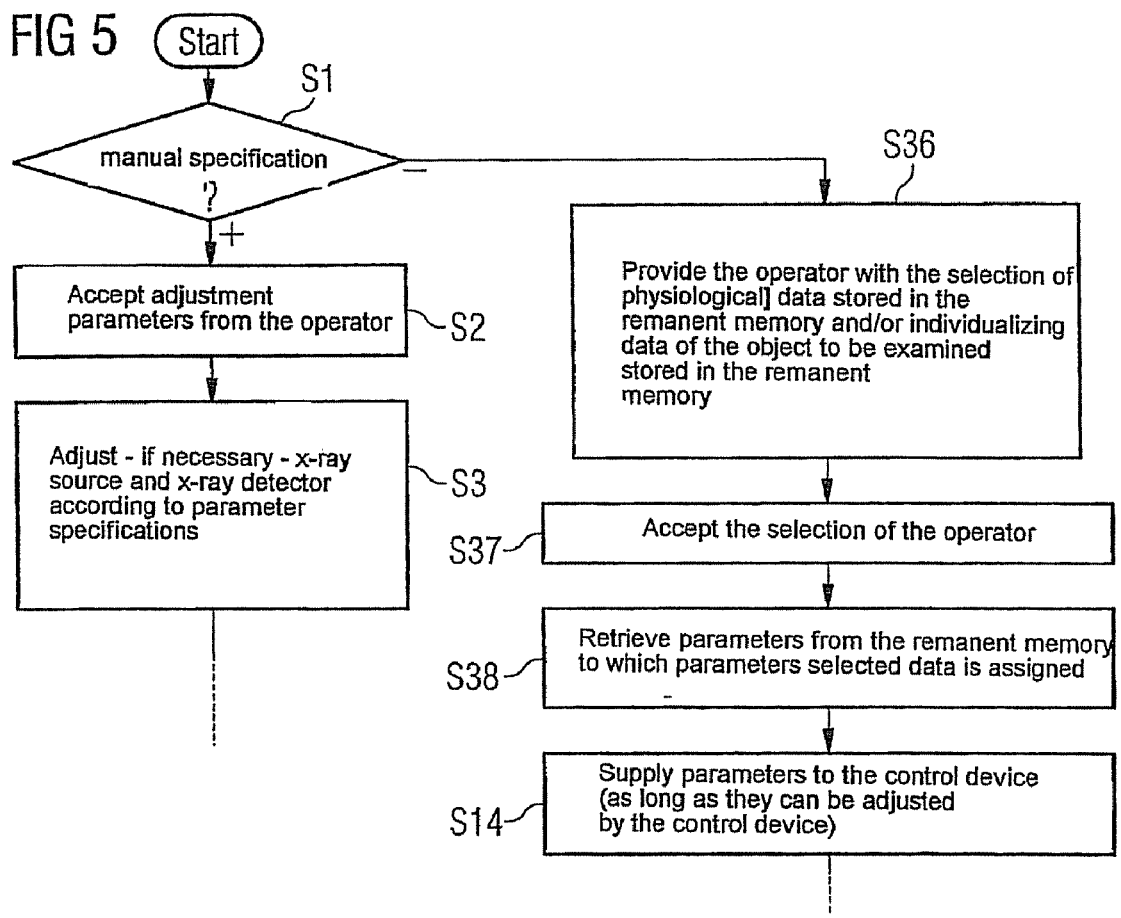
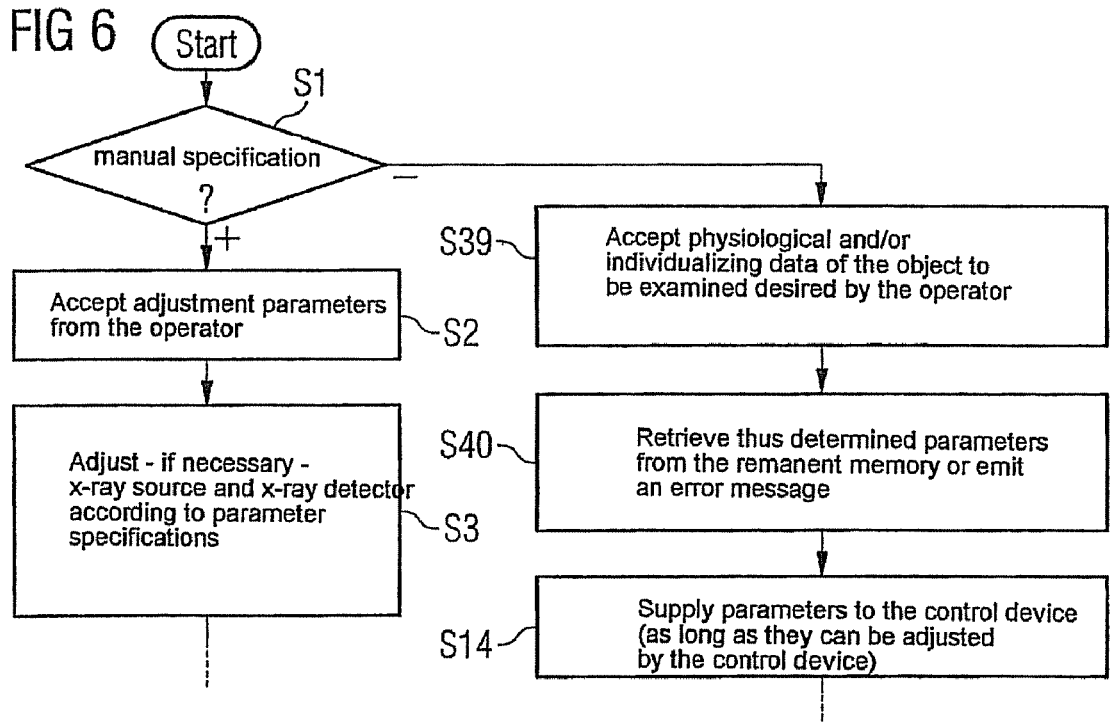

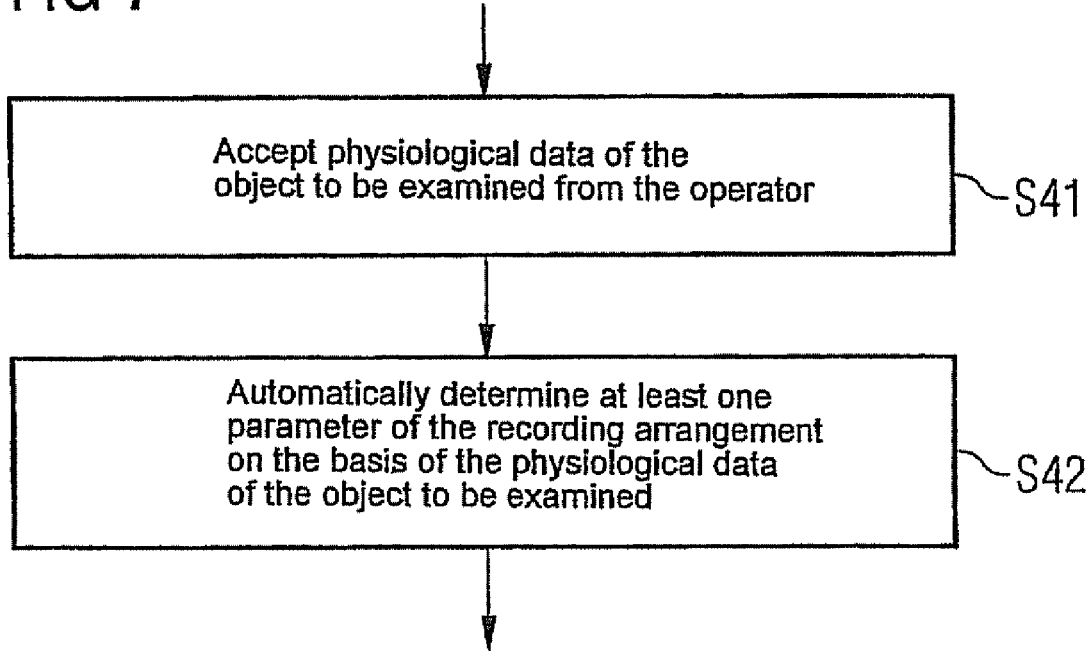
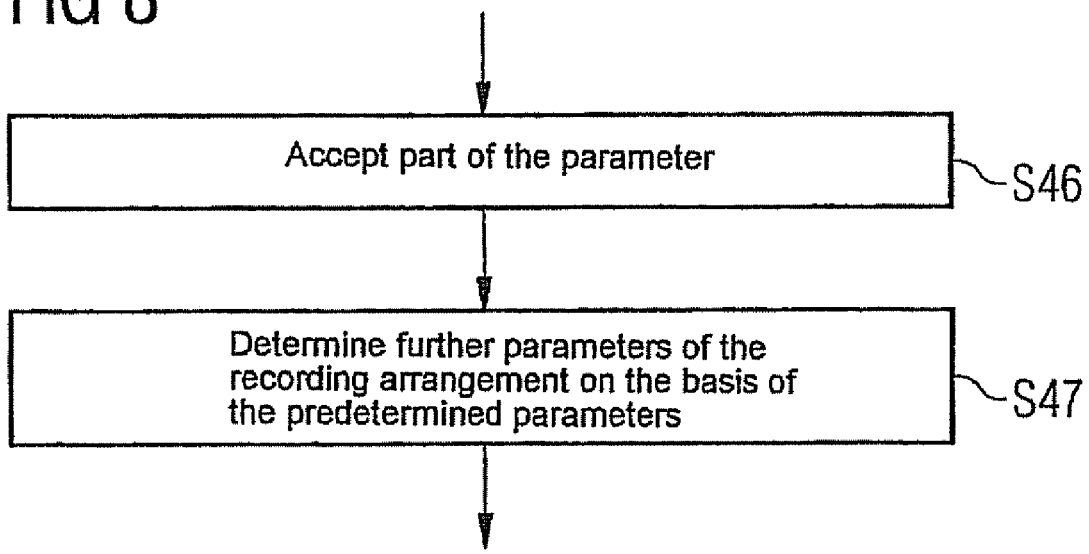

X-RAY SYSTEM WITH AN ADJUSTMENT-ACQUISITION DEVICE

CROSS REFERENCE TO RELATED APPLICATIONS

This application claims priority of German application No. 10 2006 024 973.9 filed May 29, 2006, which is incorporated by reference herein in its entirety.

FIELD OF THE INVENTION

The present invention relates to an x-ray system with a recording arrangement comprising at least one x-ray source and at least one x-ray detector.

BACKGROUND OF THE INVENTION

X-ray systems are very common. They are used with a plurality of applications, amongst others for the angiographic representation of the coronary vessel. In the context of the angiography, different analysis procedures for the acquired images are used. Examples of such analysis procedures are the determination of the flow speed of the blood in the vessels or the determination of the perfusion of the tissue supplied with blood via the vessels. With these two analysis procedures (and also with other analysis procedures) adjustment parameters are manually given to the recording arrangement by an operator of the x-ray system. The operator can provide the position of the source and/or the x-ray detector for example. Furthermore, the operator can provide a frequency and/or a trigger condition for images that can be acquired for example. The user can also provide parameters, which influence the processing of the acquired images. Depending on the given parameter the operator can for example adjust the parameters directly, provide the parameters to a control device, which controls the recording arrangement accordingly, or can provide the parameters of a processing device for the acquired images.

The x-ray source emits x-rays according to the adjustment parameters given manually. In accordance with the manually given adjustment parameters, the x-ray detector likewise respectively acquires a sequence of at least two-dimensional images of an object to be examined. The object to be examined is arranged between the x-ray source and the x-ray detector during the acquisition of the images.

The number of adjustable parameters is very large. With some of the adjustable parameters, a good or even optimal adjustment can also be achieved intuitively. For example the positioning of the x-ray source and the x-ray detector relative to the object to be examined is in many cases—but not always—relatively simple. Nevertheless, with other adjustable parameters, a good adjustment is not easily possible. In particular, the parameters often mutually influence each other. It is therefore difficult to find a good parameter combination.

A further problem consists in that in some cases, with one and the same object to be examined (e.g. with the same human), the same examination is to be carried out over larger temporal intervals. If in such a case, the adjustment parameters, with which the sequence of images is acquired and processed, vary from one examination to another, this can adversely affect the significance of the comparison of the examinations. If it is erroneously assumed that the adjustment parameters are the same, it is even possible for the examinations to be incorrectly evaluated.

A further problem consists in that in many cases more than one optimal parameter combination exists. Instead, objective and subjective factors influence whether a parameter combination is classified as good. An example of an objective factor is the used contrast means and the characteristics of the object to be examined (in particular its thickness). The individual image impression in particular is considered among the subjective factors, which the operator of the x-ray system (or another person, who examines the images) notices. It is therefore not possible to carry out an optimal adjustment of the parameters in advance.

SUMMARY OF THE INVENTION

The object of the present invention is to develop an x-ray system in such a manner that the adjustment parameters can be reproduced.

The object is achieved by an x-ray system having the features of the claims.

The x-ray system according to the invention comprises an acquisition device, by which the manually provided adjustment parameters can be acquired automatically and can be stored in a remanent memory which is at least temporarily assigned to the acquisition device, so that the stored adjustment parameters remain stored in the remanent memory after the acquisition of the sequence has concluded, irrespective of a further operation of the x-ray system. The stored adjustment parameters can be retrieved from the remanent memory by the operator of the x-ray system and can again be input into the recording arrangement, so that a further sequence of at least two-dimensional images of an object to be examined can be acquired in accordance with the adjustment parameters retrieved from the remanent memory.

The adjustment parameters can be of various natures.

It is possible for example that the adjustment parameters include source parameters, which influence the operation of the x-ray source. Examples of such parameters are the operating voltage, the operating current, the pulse duration, the pulse repetition frequency, the emitted x-ray spectrum etc.

Alternatively or in addition, it is possible that the adjustment parameters include detector parameters, which influence the operation of the x-ray detector. Examples of such parameters are the operating mode of the x-ray detector, a possible defect compensation, a pre-loading, with which the x-ray detector is operated, or a temperature of the x-ray detector.

Alternatively or in addition, it is possible that the recording arrangement comprises a processing device for processing the acquired sequence of images and that the adjustment parameters comprise processing parameters, which influence the processing of the acquired sequence of images. Examples of such parameters are the type of filtering of the acquired images, the size of a filter core, the manner of a possible averaging, the contrast adjustment etc.

Alternatively or in addition, it is possible that the recording arrangement comprises an adjustable imaging geometry and that adjustment parameters comprise geometry parameters, which correspond to the imaging geometry. Examples of such parameters are the position and/or orientation of the x-ray source, of the x-ray detector and/or the object to be examined, the arrangement of apertures in the beam path etc.

Alternatively or in addition, it is possible that the adjustment parameters comprise contrast means parameters of a contrast means used during the acquisition of the sequence. Examples of such data are the type and the quantity of the contrast means used, the temporal course of the supply of the contrast means, the location of the supply of the contrast means etc.

It is possible that the parameters retrieved from the remanent memory are output to the operator of the x-ray system and the operator carries out the adjustments. It is however preferred that the parameters retrieved from the remanent memory can at least partially be supplied by the acquisition device directly to a control device for the recording arrangement and the recording arrangement can be automatically adjusted by the control device in accordance with parameters supplied directly thereto. This procedure allows the operator to be at least partly relieved with regard to the renewed specification of the parameters regarding a laborious and error-inducing manual specification.

In an analogous manner, it is alternatively or additionally possible that the parameters retrieved from the remanent memory can be at least partially directly supplied by the acquisition device to a processing device for the newly acquired sequence of images, and the processing parameters, which influence the processing of the newly acquired sequence of images can be automatically adjusted by the processing device in accordance with the parameters directly supplied thereto. By this measure, the operator of the x-ray system is also relieved from a laborious and error-inducing manual specification of the parameters with the renewed specification of parameters.

Alternatively or in addition, it is possible that the parameters retrieved from the remanent memory can at least be partially output to the operator by the acquisition device. The output to the operator enables the operator to manually adjust the parameters. With a specification to the operator in addition to a direct specification to the control device and/or the processing device, the operator able to examine the adjustments of the parameters made automatically by the control device and/or the processing device.

It is possible that physiological data of the object to be examined can be supplied to the control device for the recording arrangement before the first specification of the adjustment parameters. Examples of such data are the age, the weight and the body mass of a patient to be examined. The supply can take place via an explicitly manual input, via automatic measurement-specific acquisition or by supplying over a data interface.

It is possible that the supply of the physiological data of the object to be examined remains without further influence. An influence is preferably given. It is possible for example that at least a part of the adjustment parameters is automatically determined by the control device on the basis of the physiological data of the object to be examined. An example of such a parameter is the radiation dosage per image. This parameter can for example be determined for example as a function of the size of the patient to be examined.

Alternatively or in addition, it is possible that the physiological data can be transferred to the acquisition device by the control device. In this case, the physiological data can be assigned to the adjustment parameters by the acquisition device and stored with the adjustment parameters.

It is furthermore—alternatively or in addition to supplying the physiological data—possible that data individualizing the object to be examined can be provided to the acquisition device, and that the acquisition device assigns the individualizing data to the adjustment parameters and stores them with the adjustment parameters.

The assigning and storing of the physiological and/or individualizing data of the object to be examined as well as the adjustment parameters can serve for different purposes. In particular it is possible that the stored adjustment parameters can be called up by the operator of the x-ray system from the remanent memory by specifying or selecting the physiological and/or the individualizing data of the object to be examined. In particular the assignment of the individualizing data enables a subsequent acquisition of a sequence by identically adjusting the x-ray system.

It is possible that with the manual specification, all adjustment parameters are manually provided to the control device. Alternatively it is possible with the manual specification that only one part of the adjustment parameters is provided to the control device. On the basis of the given part of the adjustment parameters, the control device can in this case automatically determine the remaining adjustment parameters. By way of example, an operating voltage of the x-ray source can be automatically determined as a function of the contrast means used and possibly also adjusted. The specification of a contrast means quantity can likewise influence threshold values for a subsequent image evaluation.

BRIEF DESCRIPTION OF THE DRAWINGS

Further advantages and details emerge from the following description of exemplary embodiments in conjunction with the drawings, in which;

FIG. 1 shows a detailed description of an x-ray system and FIGS. 2 to 8 show detailed flow charts.

DETAILED DESCRIPTION OF THE INVENTION

Figure 1:
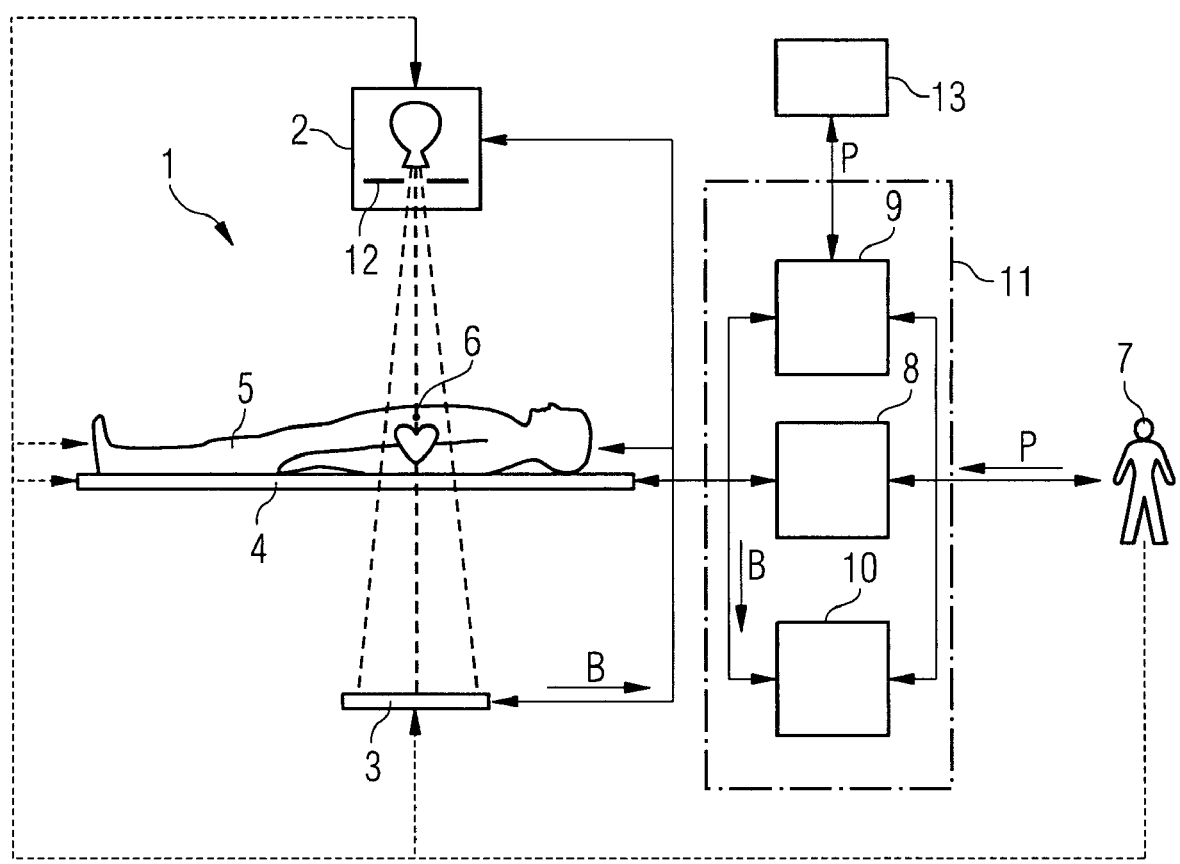

According to FIG. 1, an x-ray system comprises a recording arrangement 1. The recording arrangement 1 comprises at least an x-ray source 2 and an x-ray detector 3. The recording arrangement 1 furthermore generally comprises a patient bed 4, on which an object 5 to be examined can be arranged. The object 5 to be examined is usually a human.

If necessary, the recording arrangement 1 can comprise further x-ray sources in addition to the x-ray source 2 shown in FIG. 1. In this case further x-ray detectors are present, not shown in FIG. 1, that is one further x-ray detector for each further x-ray source.

The x-ray source 2 and the x-ray detector 3 can be arranged in a stationary manner. They are usually arranged in a movable manner. The degree of mobility can vary widely. In the simplest case, the x-ray source 2 and the x-ray detector 3 can only be moved together. By way of example, they can comprise a single common translational or rotary degree of freedom. In this case, only a common movement of the x-ray source 2 and the x-ray detector 3 is possible. For example, with a C-curved x-ray system, only a common swiveling of the x-ray source 2 and the x-ray detector 3 is possible around a common swivel axis 6. In other cases, the x-ray source 2 and the x-ray detector 3 can be positioned completely independently of one another in up to three translational directions respectively and up to three rotary orientations respectively.

If a positioning of the x-ray source 2 and of the x-ray detector 3 is possible, the positioning can take place directly by means of an operator 7 of the x-ray system. Alternatively, the positioning can take place by means of control device 8, which controls corresponding actuating elements. During the positioning by the control device 8, the control device 8 controls the recording arrangement 1 according to geometry parameters, which are given to the control device 8 by the operator 7 directly or indirectly. Independently of the degree of the mobility and independently of the exact type of the positioning, the positioning of the x-ray source 2 and of the x-ray detector 3 relative to the patient bed 4 always takes place in such a manner that the object 5 to be examined—or the relevant part of the object 5 to be examined—is arranged between the x-ray source 2 and the x-ray detector 3.

The x-ray system comprises an acquisition device 9 in addition to the control device 8. Furthermore, it can comprise a processing device 10. It is possible that the control device 8, the acquisition device 9, and the processing device 10 are combined to form a common computing device 11. Alternatively, they can be devices which differ from one another.

In the following, a distinction is made between the functions executed by the control device 8, the acquisition device 9 and by the processing device 10. This only takes place in order to represent more clearly which of the devices 8, 9, 10 realizes which functions. The combination of the devices 8, 9, 10 into the common computing device 11 should thereby not be excluded.

The basic principle of the present invention is described in more detail below in conjunction with FIG. 2. FIG. 2 shows a flow chart for the computing device 11. It is however always stated whether the respective function of the computing device 11 is carried out by the control device 8, of the acquisition device 9 or of the processing device 10 is executed. Furthermore, FIG. 1 is also to be included in connection with the explanation of FIG. 2.

In accordance with FIG. 2, the control device 8 examines in step S1 whether the operator 7 has given a command for the manual specification of adjustment parameters P. Which parameters are applicable as adjustment parameter P is subsequently described in more detail.

In step S2, the control device 8 accepts the adjustment parameters P, which are manually given to it by the operator 7. The term "manual specification" means in this connection that the operator 7 makes the appropriate input. The manner in which he does this is not important within the context of step S2. It is only important that it does not concern adjustments that the control device 8 makes automatically.

In step S3, the control device 8 adjusts the x-ray source 2 and the x-ray detector 3 according to the parameter specifications having taken place in the step S2, as far as this is already useful. An aperture device 12 of the x-ray source 2 can be adjusted for example. If necessary, the positioning can also already take place.

In step S4, the processing device 10 accepts parameters, which are manually given to it by the operator 7—directly or via the control device 8—. The term "manual specification" within this context has the same meaning as in the context of the step S2.

In step S5, the processing device 10 adjusts processing parameters, which influence the processing of the sequence of images B still to be acquired, according to the parameters, which were given to it by the operator 7 within the context of the step S4.

In step S6, the control device 8 waits for the operator 7 to give it a starting signal. If the control device 8 has accepted the starting signal, the control device 8 sends an activation signal to the acquisition device 9. The acquisition device 9 thereupon automatically acquires the adjustment parameters P of the x-ray system, i.e. without interaction from the operator 7.

If the adjustment parameters P are values, which the operator 7 has provided to the control device 8 and/or the processing device 10, only a transmission of the corresponding values from the control device 8 and/or the processing device 10 to the acquisition device 9 is necessary. The transmission can alternatively be activated by the acquisition device 9 or by the control device 8 or the processing device 10. These values are taken over by the acquisition device 9 in step S7.

With regard to adjustment parameters P, which the operator 7 has adjusted without interaction from the control device 8 and/or the processing device 10—for example the positioning of the x-ray source 2 and/or the x-ray detector 3—corresponding sensors which acquire these parameters P are assigned to the acquisition device 9. Regarding these parameters P, the acquisition device 9 automatically controls the corresponding sensors in step S8 and takes over their measured values. These sensors are not shown in FIG. 1 for the sake of clarity.

The acquisition device 9 stores the parameters P acquired in steps S7 and S8 in step S9 in a remanent memory 13. The remanent memory 13 is formed in such a manner that the parameters P stored therein remain stored independently of a further operation of the x-ray system. In particular, the parameters P also remain when an external power supply of the x-ray system is switched off. The switching off of the power supply can take place for example after the termination of the flow chart of FIG. 2.

The remanent memory 13 can for example be formed as a buffered RAM, EEPROM, as a magnetic memory (e.g. as a floppy disc or as a hard drive) or as an optical memory (e.g. as a recordable CD-ROM). It can be permanently assigned to the acquisition device 9, e.g. be formed as a permanently installed hard drive or as an internal, battery-buffered RAM. The remanent memory 13 can alternatively be assigned only temporarily to the acquisition device 9; it can for example be formed as a floppy disc, as a CD-ROM or as an USB stick.

In step S10, the control device 8 controls the recording arrangement 1. In particular, the control device 8 controls the x-ray source 2 according to parameters given in step S2. The x-ray source 2 therefore emits x-rays in accordance with the parameters P x-ray given in the step S2.

The control device 8 further controls the x-ray detector 3 within the context of step S10 in accordance with the parameters P given in step S2. The x-ray detector 3 therefore acquires a sequence of two-dimensional (in individual cases also three-dimensional) images B of the object 5 to be examined in accordance with the parameters P given in step S2.

The acquired sequence of images B is supplied to the processing device 10, directly or indirectly via the control device 8. The processing device 10 processes the sequence of images B in step S11. The processing takes place according to the parameters P, which the operator 7 has given in the step S2.

If the operator 7 did not select the manual specification of the parameters P in step S1, the acquisition device 9 accepts a retrieval command for the parameters P stored in the remanent memory 13 from the operator 7 in step S12. If necessary, a previous selection or choice can take place. This is still explained below. In step S13, the acquisition device 9 retrieves the parameters P stored in the remanent memory 13 from the remanent memory 13.

As far as the parameters P can be adjusted by the control device 8, the acquisition device 9 supplies the relevant parameters P directly to the control device 8 in step S14. The control device 8 is thereby able to automatically adjust the recording arrangement 1 in step S15 in accordance with the parameters P directly supplied thereto. An interaction of the operator 7 is not necessary.

As far as the parameters P concern the processing device 10, the acquisition device 9 supplies the corresponding parameters P preferably directly to the processing device 10 in step S16. The processing device 10 is therewith able to automatically adjust the corresponding parameters P, which concern the processing of the acquired sequence of images B, in step S17 in accordance with the parameters P directly supplied thereto.

In step S18, the acquisition device 9 outputs the parameters P retrieved from the remanent memory 13 to the operator 7. As far as the parameters P of the control device 8 and/or of the processing device 10 are not supplied, the output to the operator 7 is compulsory. Because in this case, the operator 7 has to perceive and manually adjust the corresponding parameters P intellectually. As far as parameters P are concerned, which are supplied directly to the control device 8 and/or the processing device 10, the output to the operator 7 is not compellingly necessary. It is however also useful for these parameters P. Because it is thus made possible for the operator 7 to examine whether the control device 8 and/or the processing device 10 have correctly adopted and adjusted the parameters P supplied to them.

In step S19, the control device 8 and/or the processing device 10 accept changes or other inputs of the parameter P intended for them from the operator 7.

The remaining execution of the method of FIG. 2 takes place as described above. Step S9 is only implemented if the operator 7 has changed parameters P in step S19 or if a renewed storage is necessary for other reasons.

Independent of whether the renewed specification of the parameters P stored in the remanent memory 13 takes place automatically (steps S14 to S17) or (completely or partially) by interposition of the operator 7 (steps S18 and S19), it is possible due to the step S13 to again input exactly the same adjustment parameters P to the recording arrangement 1. A further sequence (at least) of two-dimensional images B of the same or another object 5 to be examined can therefore be acquired and evaluated with the same parameters P, with which the first sequence of images B was acquired.

The basic principle of the present invention explained above in conjunction with FIG. 1 and 2 can be formed in different ways. This is explained in more detail below in conjunction with FIG. 3 to 8.

According to FIG. 3, the parameters P, which are given manually by the operator 7 within the context of step S2, can be of various natures.

The parameters P can for example comprise geometry parameters, which influence the imaging geometry of the recording arrangement 1. Examples of geometry parameters are the positions of the x-ray source 2, the x-ray detector 3, the patient bed 4 and the object 5 to be examined. Further geometry parameters are the arrangement and positioning of possible apertures of the aperture arrangement 12 in the beam path etc. These parameters P are possibly provided by the operator 7 in step S21.

The geometry parameters can be static, i.e. remain unchanged during the acquisition of the sequence of images B. In this case it is possible for the operator 7 to adjust the geometry parameters (in the literal sense) manually himself, that is, to make these adjustments himself without interposition of the control device 8. Alternatively, the operator 7 can provide the geometry parameters of the control device 8. In this case, the control device 8 controls the recording arrangement 1 accordingly, so that the geometry parameters are adjusted.

During the adjustment of the geometry parameters by the control device 8 the geometry parameters do not have to be static, even if this is naturally possible. The geometry parameters can alternatively be dynamic during the adjustment by the control device 8, that is, can be changed during the acquisition of the sequence of images B.

The adjustment of the geometry parameters by the control device 8 is preferential. In accordance with FIG. 3 a step S22 is therefore present, in which the control device 8 adjusts the imaging geometry according to the geometry parameters given in step S21.

Alternatively or in addition, the parameters P can comprise source parameters, which influence the operation of the x-ray source 2. Examples of such source parameters are the operating voltage and the operating current of the x-ray source 2, the pulse repetition frequency, the duration of an individual pulse, the desired x-ray spectrum, the desired x-ray intensity etc. These parameters are if necessary given to the control device 8 by the operator 7 in a step S23. The control device 8 controls in this case in a step S24 the x-ray source 2 according to the given source parameters, so that the x-ray source 2 emits X-rays according to the source parameters.

Alternatively or in addition, the parameters P can comprise detector parameters, which influence the operation of the x-ray detector 3. Examples of such detector parameters are the operating mode and the operating temperature of the x-ray detector 3, the activation cycle of the x-ray detector 3, a possible detector pre-load, the type of the defect compensation etc. These parameters are if necessary supplied to the control device 8 by the operator 7 in step S25. In a step S26, the control device in this case 8 controls the x-ray detector 3 according to the detector parameters, so that the x-ray detector 3 acquires the images B according to the given detector parameters.

Alternatively or in addition, the parameters P can comprise processing parameters, which influence the processing of the acquired sequence of images B. Examples of processing parameters are the type of the filtering of the acquired images B, the size of the filter core, the type of averaging, the contrast adjustment etc.

If the processing is an image-spanning processing of the entire sequence (for example a perfusion analysis or a determination of a flow speed), the processing parameters can alternatively or additionally comprise values, which are of importance within the context of this image-spanning processing. For example threshold values can be provided, on the basis of which the processing device 10 determines whether one of the types vessel, perfusion range or background is assigned to a certain pixel of the images B, and which perfusion degree is assigned to a pixel of the type perfusion range. Such determination methods are for example disclosed in the older German patent application 10 2005 039 189.3 of the applicant, not published on application date of the present invention.

The parameters concerning the processing of the images B are possibly input to the processing device 10 by the operator 7 in step S27. In this case, the processing device 10 undertakes the processing of the acquired sequence of images B in a step S28 corresponding to the processing parameters given in step S27.

Alternatively or in addition, the parameters P can comprise contrast means parameters. Examples of such parameters are the type of the contrast means used, the quantity of the contrast means used, the temporal course of the supply of the contrast means, the supply location etc. The contrast means parameters are possibly given to the control device 8 by the operator 7 in step S29. The control device 8 undertakes in this case the supply of the contrast means in a step S30 according to the temporal course given in the step S29. It can also ensure that the total contrast means quantity used corresponds to the contrast means quantity given in step S29. The location of the supply of the contrast means and the selection of the contrast means itself must usually be carried out by the operator 7.

The parameters P described above are purely exemplary. It is generally valid that the sequence of images B can be acquired in a more reproducible and processable manner, the more the parameters are adjusted reproducibly.

The parameters P stored in the remanent memory 13 should preferably not only be retrievable again. They should rather also preferably have the ability to be allocated correctly. In the simplest case, a simple numbering is sufficient for the assignment (parameter set 1, parameter set 2, . . . ) and/or a time allocation (e.g. parameter set of date 1 and of time 1, parameter set of date 2 and of time 2, . . . ) or the like. An assignment preferably takes place, as is described below in conjunction with FIG. 4.

In accordance with FIG. 4, steps S31 and S32 (or before step S21 of FIG. 3) can be inserted before step S2 of FIG. 2. In step S31, data which individualizes the object 5 to be examined is given to the control device 8 by the operator 7. Examples of such data are the name and the first name in connection with a date of birth, an identification number and so on. In step S32, physiological data of the object 5 to be examined is supplied to the control device 8. Examples of such data are the age, the size, the weight and possibly also the sex of the object 5 to be examined.

The specification of the physiological and/or the individualizing data of the object 5 to be examined can take place in different ways. The simplest is a manual input by the operator 7, for example via a corresponding input mask, which outputs the control device 8 over a display device to the operator 7. Alternatively, the physiological and/or individualizing data can be supplied to the control device 8 via an interface from another computer. The physiological data can alternatively be automatically acquired by the control device 8. For example the weight of the object 5 to be examined can be automatically acquired by the control device 8 by means of a simple weight sensor.

If the physiological and/or individualizing data of the object 5 to be examined is supplied to the control device 8, steps S7 and S9 of FIG. 2 are preferably slightly modified. They are therefore referred to as steps S7' and S9' in FIG. 4.

In addition to the parameters P manually provided thereto, the control device 8 also transfers, in step S7', the physiological and/or individualizing data of the object 5 to be examined provided thereto, to the acquisition device 9. In step S9', the acquisition device 9 assigns the physiological and/or individualizing data of the object 5 to be examined provided to it to the parameters P acquired therefrom and stores them together with the parameters P in the remanent memory 13.

Due to the allocation of the physiological and/or the individualizing data of the object 5 to be examined (see FIG. 4), the retrieval of the parameters P stored in the remanent memory 13 can be realized in accordance with FIG. 5 for example as follows:

In step S36 the acquisition device 9 offers the physiological data stored in the remanent memory 13 and/or the individualizing data of the object 5 to be examined stored in the remanent memory 13 to the operator 7 for selection. The operator 7 can for example alphabetically leaf through the individualizing data of objects 5 to be examined. In step S37, the acquisition device 9 accepts a selection from the operator 7. In step S38, the acquisition device 9 retrieves those of the stored parameters P from the remanent memory 13, which are assigned to the data selected in step S37.

Alternatively to the proceedings of FIG. 5, it is possible in accordance with FIG. 6 to replace steps S36 and S37 by step S39. In step S39, the operator 7 supplies the physiological and/or the individualizing data desired by him to the acquisition device 9. In this case, either the acquisition device 9 retrieves the parameters P determined in such a way from the remanent memory 13 in step S40 or an error message takes place.

The proceedings of FIG. 4 to 6 can be realized alternatively or additionally to the proceedings of the FIG. 3.

In connection with FIG. 7 and 8, further configurations of the present invention are described below. These two configurations can be realized alternatively individually or together. Furthermore they can be realized alternatively or together with the embodiments of FIGS. 3, 4 to 6 or 3 to 6.

In accordance with FIG. 7, the physiological data of the object 5 to be examined is supplied to the control device 8 by the operator 7 in step S41. Step S41 can be combined with step S32 of FIG. 4.

In step S42, the control device 8 automatically determines at least one of the parameters P of the recording arrangement 1 on the basis of the physiological data of the object 5 to be examined. For example the control device 8 can automatically determine an x-ray dose on the basis of the thickness of the object 5 to be examined, which is optimal for the acquisition of an individual image from images B. Alternatively or in addition for example a pre-positioning—possibly even a complete positioning—of the x-ray source 2, the x-ray detector 3, the patient bed 4 etc. can be determined, and can possibly even be adjusted on the basis of the findings of the medical condition. By the proceedings in accordance with FIG. 7, the operator 7 is partially relieved from a manual input of parameters P to be adjusted.

In accordance with FIG. 8, a part of the parameters P is given to the control device 8 in step S46. Step S46 thus corresponds to a part of step S2 of FIG. 2 or a part of step S21, S23, S25, S27 and S29 of FIG. 3.

In step 47, the control device 8 determines further parameters P of the recording arrangement on the basis the parameters P given in step S46. Similar to FIG. 7, the operator 7 is also partly relieved of the manual input of the parameters P in this case.

Within the context of step S47, the control device 8 can for example determine threshold values for an evaluation of the sequence of images B on the basis of the given contrast means quantity. Alternatively or additionally it can determine the operating voltage, the operating current, the x-ray spectrum and the x-ray dose. With the determination of these values, the type of contrast means can alternatively or additionally be considered. It is also possible to determine threshold values for the later processing of the recorded images on the basis of a given dose per image and/or the x-ray spectrum.

By means of the present invention, a reproducible operation of the x-ray system is possible in a simple manner.

The above description only serves to explain the present invention. The scope of protection of the present invention is however to be exclusively determined by the attached claims.

The invention claimed is:

1. An x-ray system for performing a medical examination, comprising:
   an x-ray source that emits x-rays according to a plurality of adjustment parameters manually supplied to the x-ray system by an operator of the x-ray system;
   an x-ray detector that acquires a first sequence of images of a patient in accordance with the plurality of adjustment parameters;
   a remanent memory that stores and continues to store the plurality of adjustment parameters after a power shut down of the x-ray system; and
   an acquisition device that automatically retrieves the plurality of adjustment parameters from the remanent memory when the x-ray system is powered up for acquiring a further sequence of images of the same patient after the power shut down of the x-ray system, wherein at least some of the plurality of retrieved adjustment parameters are outputted to the operator, wherein at least one of the outputted adjustment parameters is manually adjusted by the operator, wherein the retrieved adjustment parameters together with said at least one manually adjusted parameter constitute an updated plurality of adjustment parameters, wherein the updated plurality of adjustment parameters is supplied to the x-ray system for acquiring the further sequence of images of the same patient, wherein at least one of the plurality of adjustment parameters comprises a detector parameter that controls an operation of the x-ray detector, wherein at least one of the plurality of adjustment parameters further comprises a contrast medium parameter of a contrast medium used during acquiring the sequence of images.

2. The x-ray system as claimed in claim 1, wherein at least one of the adjustment parameters comprises a source parameter that controls an operation of the x-ray source.

3. The x-ray system as claimed in claim 1, wherein at least one of the adjustment parameters comprises a processing parameter that controls a processing of the acquired sequence of images.

4. The x-ray system as claimed in claim 1, wherein at least one of the adjustment parameters comprises a geometry parameter that controls an imaging geometry of the x-ray system.

5. The x-ray system as claimed in claim 1, wherein the retrieved plurality of adjustment parameters is at least partially supplied to a control device of the x-ray system and the x-ray system is automatically adjusted by the control device according to the retrieved plurality of adjustment parameters.

6. The x-ray system as claimed in claim 1, wherein the retrieved plurality of adjustment parameters is at least partially supplied to a processing device of the x-ray system and the further acquired sequence of images is processed by the processing device according to the retrieved plurality of adjustment parameters.

7. The x-ray system as claimed in claim 1, wherein the retrieved plurality of adjustment parameters is at least partially outputted to the operator and the x-ray system is manually adjusted by the operator according to the retrieved plurality of adjustment parameters.

8. The x-ray system as claimed in claim 1, wherein a physiological data of the patient is supplied to a control device of the x-ray system before the plurality of adjustment parameters is manually supplied to the x-ray system by the operator.

9. The x-ray system as claimed in claim 8, wherein at least a part of the plurality of adjustment parameters is automatically determined by the control device based on the physiological data of the patient.

10. The x-ray system as claimed in claim 9, wherein the physiological data of the patient is transferred to the acquisition device by the control device and assigned to the plurality of adjustment parameters by the acquisition device and stored with the plurality of adjustment parameters.

11. The x-ray system as claimed in claim 10, wherein an individual data of the patient is supplied to the acquisition device and assigned to the plurality of adjustment parameters by the acquisition device and stored with the plurality of adjustment parameters.

12. The x-ray system as claimed in claim 11, wherein the plurality of adjustment parameters is retrieved from the remanent memory by specifying or selecting the physiological or the individual data of the object.

13. The x-ray system as claimed in claim 1, wherein a part of the plurality of adjustment parameters is manually supplied to a control device of the x-ray system by the operator and a remaining part of the plurality of adjustment parameters is automatically determined by the control device based on the manually supplied part of the adjustment parameters.

14. An x-ray system for performing a medical examination, comprising:
an x-ray source that emits x-rays according to a plurality of adjustment parameters manually supplied to the x-ray system by an operator of the x-ray system;
an x-ray detector that acquires a first sequence of images of a patient in accordance with the plurality of adjustment parameters;
a remanent memory that stores and continues to store the plurality of adjustment parameters after a power shut down of the x-ray system; and
an acquisition device that automatically retrieves the plurality of adjustment parameters from the remanent memory when the x-ray system is powered up for acquiring a further sequence of images of the same patient, wherein at least some of the plurality of retrieved adjustment parameters are outputted to the operator, wherein at least one of the outputted adjustment parameters is manually adjusted by the operator, wherein the retrieved adjustment parameters together with said at least one manually adjusted parameter constitute an updated plurality of adjustment parameters, wherein the updated plurality of adjustment parameters is supplied to the x-ray system for acquiring the further sequence of images of the same patient, wherein at least one of the adjustment parameters comprises a detector parameter that controls an operation of the x-ray detector, and further wherein the acquisition device receives a command from the operator for automatically retrieving the plurality of adjustment parameters from the remanent memory.

15. A method for operating an x-ray system, comprising:
manually supplying a plurality of adjustment parameters to the x-ray system by an operator of the x-ray system;
emitting x-rays by an x-ray source of the x-ray system according to the plurality of adjustment parameters;
acquiring a first sequence of images of a patient by x-ray detector of the x-ray system in accordance with the plurality of adjustment parameters;
storing the adjustment parameter in a remanent memory;
continuing to store the plurality of adjustment parameters after a power shut down of the x-ray system;
when the x-ray system is powered up for acquiring a further sequence of images of the same patient after the power shut down of the x-ray system, automatically retrieving the plurality of adjustment parameters from the remanent memory by an acquisition device of the x-ray system;
supplying the retrieved adjustment parameter to the x-ray system;
outputting at least some of the plurality of retrieved adjustment parameters to the operator;
manually adjusting by the operator at least one of the outputted adjustment parameters, wherein the retrieved adjustment parameters together with said at least one manually adjusted parameter constituting an updated plurality of adjustment parameters; and supplying the updated plurality of adjustment parameters to the x-ray system for acquiring the further sequence of images of the same patient, wherein at least one of the adjustment parameters comprises a detector parameter that controls an operation of an x-ray detector responsive to the x-rays emitted by the x-ray source, and wherein at least one of the adjustment parameters further comprises a contrast medium parameter of a contrast medium used during acquiring the sequence of images.

16. The method as claimed in claim 15, wherein a part of the plurality of adjustment parameters is manually supplied to a control device of the x-ray system by the operator and a remaining part of the plurality of adjustment parameters is automatically determined by the control device based on the manually supplied part of the adjustment parameters.

17. The method as claimed in claim 15, wherein the acquisition device receives a command from the operator for automatically retrieving the plurality of adjustment parameters from the remanent memory.

* * * * *